US00PP30757P2

(12) United States Plant Patent
van den Heever

(10) Patent No.: US PP30,757 P2
(45) Date of Patent: Jul. 30, 2019

(54) MANGO TREE NAMED 'TROPICA'

(50) Latin Name: ***Mangifera indica* L.**
Varietal Denomination: Tropica

(71) Applicant: Frans Albertus van den Heever, Clanwilliam (ZA)

(72) Inventor: Frans Albertus van den Heever, Clanwilliam (ZA)

( * ) Notice: Subject to any disclaimer, the term of this patent is extended or adjusted under 35 U.S.C. 154(b) by 0 days.

(21) Appl. No.: 15/732,808

(22) Filed: Dec. 28, 2017

(51) Int. Cl.
*A01H 5/08* (2018.01)

(52) U.S. Cl.
USPC ..... Plt./159
CPC ..... *A01H 5/08* (2013.01)

(58) Field of Classification Search
USPC ..... Plt./159
CPC ..... A01H 5/08
See application file for complete search history.

*Primary Examiner* — Kent L Bell
(74) *Attorney, Agent, or Firm* — Michelle Bos Legal LLC

(57) ABSTRACT

'Tropica' mango (*Mangifera indica* L.) is a new mango variety of unknown parentage notable for its high quality fruit, which is well suited for shipping and fresh eating.

6 Drawing Sheets genus and species: *Mangifera indica* L.
Variety denomination: 'Tropica'.

CROSS-REFERENCE TO RELATED APPLICATIONS

None

BACKGROUND AND SUMMARY OF THE VARIETY

The new mango tree 'Tropica', which originated as a chance seedling of unknown parentage, was discovered by the inventor in a cultivated orchard in Clanwilliam, South Africa. 'Tropica' was selected for further observation due to the desirable qualities of its fruit. 'Tropica' has been asexually propagated by grafting in South Africa and has been observed to reproduce true-to-type over successive asexually propagated generations.

Although the parentage of 'Tropica' is unknown, the inventor believes the parentage of his new variety may include 'Heidi' (not patented) and 'Sensation' (not patented) mango varieties. As compared to 'Heidi', 'Tropica' has a less sensitive skin that makes it more suitable for shipping. 'Tropica' does not have the internal quality problems sometimes found in 'Sensation'.

BRIEF DESCRIPTION OF THE PHOTOGRAPHS

Figure 1:
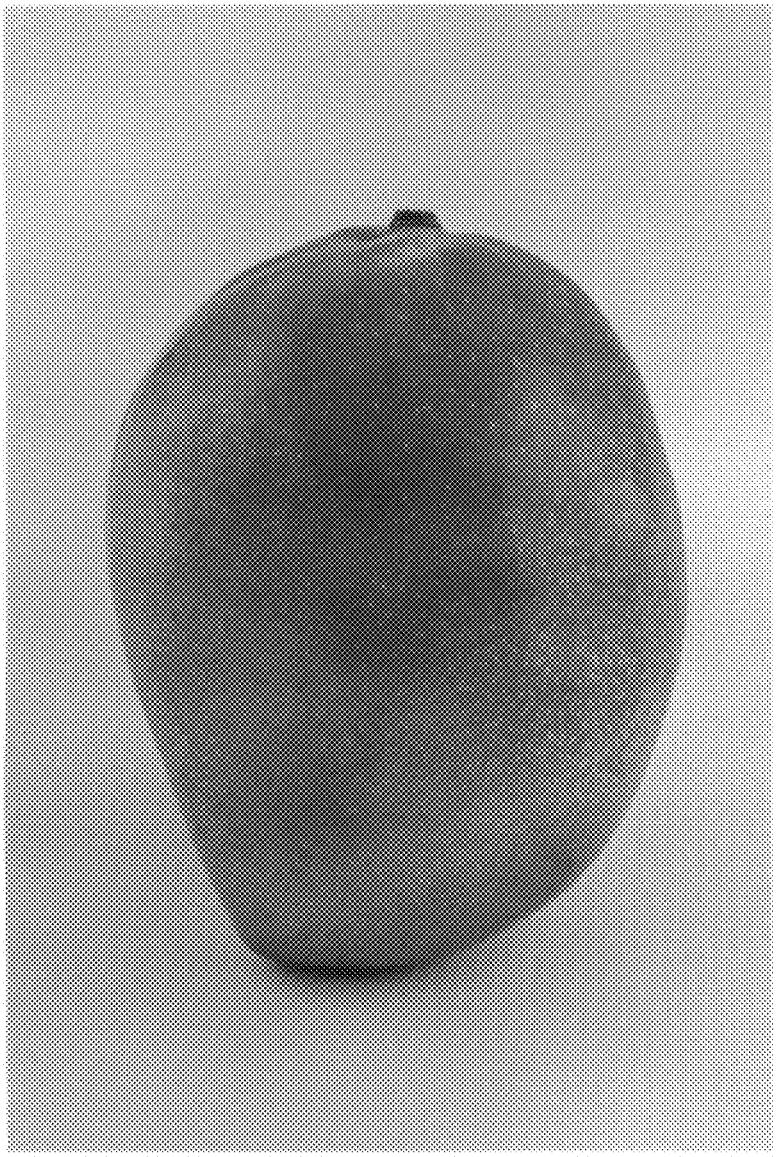
Figure 2:
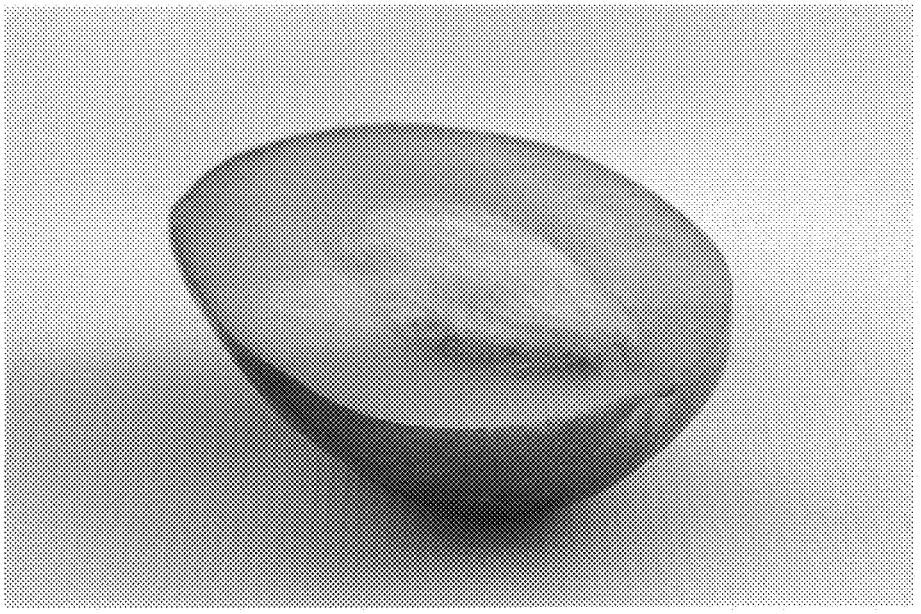
Figure 3:
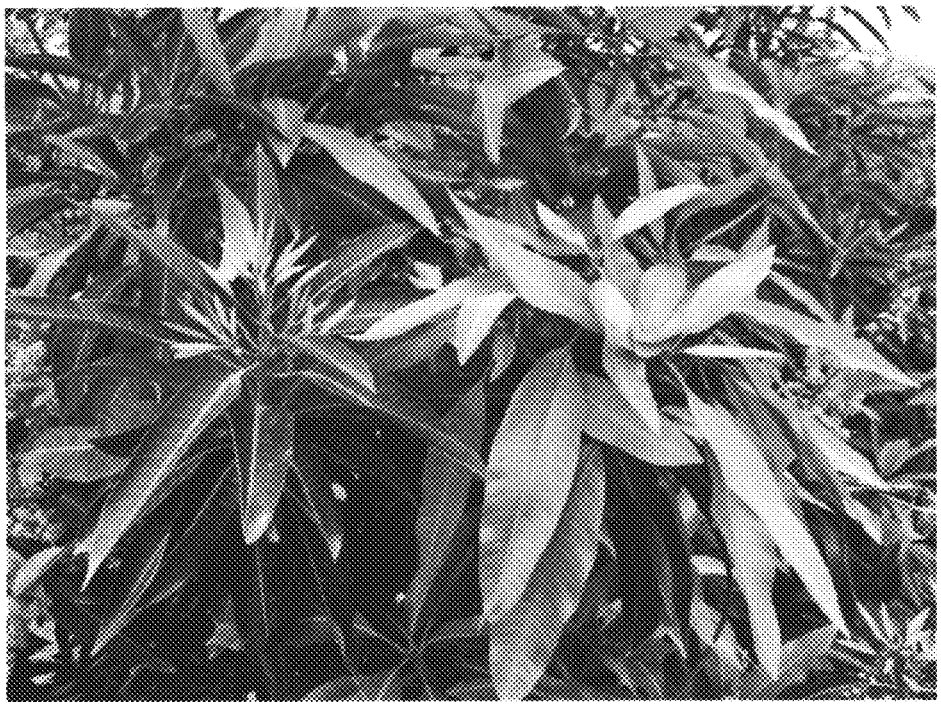
Figure 4:
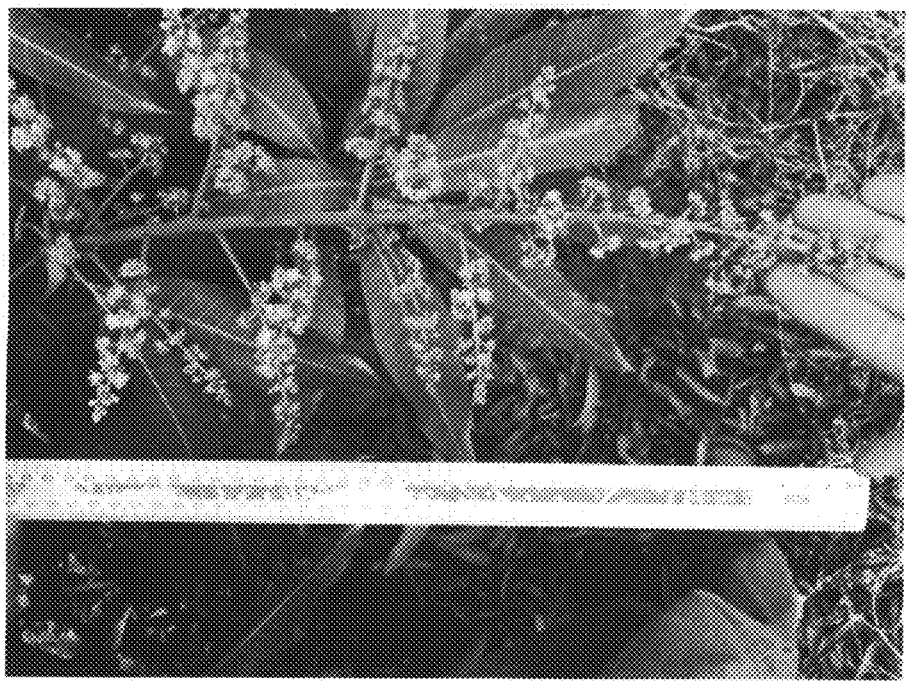
Figure 5:
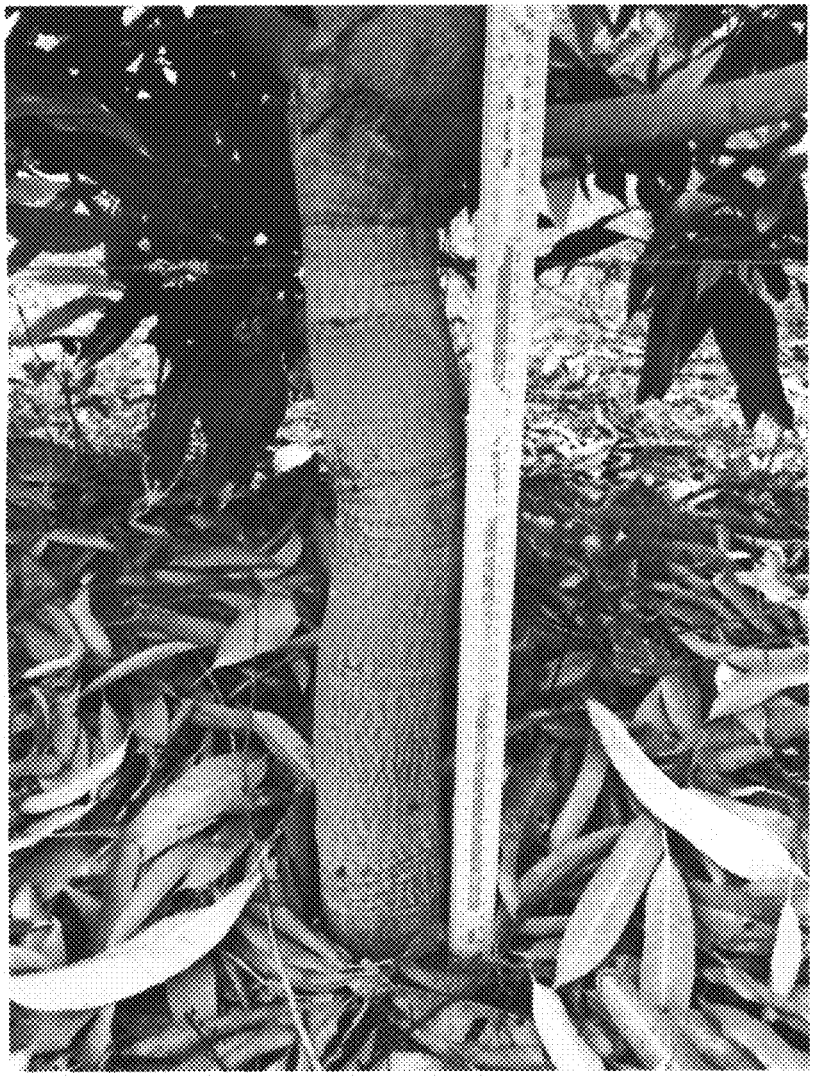
Figure 6:
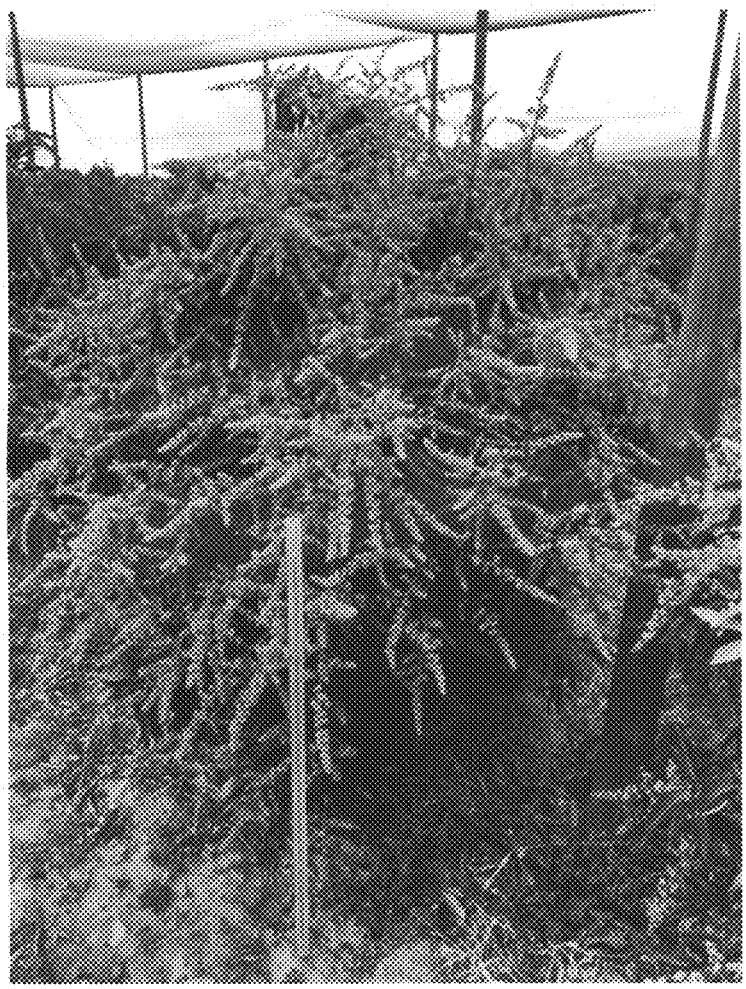

FIG. 1 shows ripe fruit of the 'Tropica' mango variety;
FIG. 2 shows sectioned ripe fruit of the 'Tropica' mango variety;
FIG. 3 shows leaves on a 'Tropica' mango tree;
FIG. 4 shows an inflorescence on a 'Tropica' mango tree;
FIG. 5 shows the trunk of a 'Tropica' mango tree; and
FIG. 6 shows a 'Tropica' mango tree.

The colors of the claimed variety may vary with lighting conditions. Color characteristics of the variety should therefore be determined with reference to the observations described herein, rather than from these illustrations alone.

DETAILED BOTANICAL DESCRIPTION

The following detailed botanical description is based on observations of 6-year-old trees, recorded during the 2017 growing season at Clanwilliam, South Africa. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants of the new variety may vary from the stated average. Colors are described with reference to The Royal Horticultural Society Colour Chart.

Tree:
- *Vigor.*—Stronger than average.
- *Height.*—Medium to large, 3 m.
- *Spread.*—2 m.
- *Growth habit.*—Erect to slightly spreading.
- *Productivity.*—Heavy, regular bearer.
- *Trunk diameter.*—18 cm at base.
- *Bark texture.*—Smooth to medium.
- *Bark color.*—Grey-brown 199B to 199C.

Branches:
- *Bark color.*—Grey-brown 199B to 199C.
- *Bark texture.*—Smooth to medium.
- *Diameter.*—10 cm (primary branches).

Inflorescence:
- *Number of years to first flowering.*—2 years.
- *Regularity of flowering.*—Every year.
- *Bloom date.*—August to October.
- *Form.*—Panicle.
- *Inflorescence position.*—Apical.
- *Axis growth habit.*—Semi-erect.
- *Shape.*—Conical.
- *Length.*—44 cm.
- *Width.*—35 cm.

*Flowers per inflorescence.*—Up to about 2000.
*Peduncle color.*—Red-purple 58C and 58D.
*Peduncle length.*—35 cm to 38 cm.
*Peduncle diameter.*—6 mm.
*Pubescence.*—Sparse, very fine.
*Presence of leafy bracts.*—Absent.
*Density of flowers.*—Medium.

Flower:
*Flower bud shape.*—Conical.
*Flower bud length.*—3 mm to 4 mm.
*Flower bud diameter.*—2 mm to 3 mm.
*Flower bud color.*—Light yellow green 145D.
*Type of flower.*—Hermaphrodite; about 70% male and 30% female.
*Flower height.*—10 mm.
*Flower diameter.*—8 mm to 10 mm.
*Flower fragrance.*—Pungent.
*Pedicel length.*—5 mm.
*Pedicel diameter.*—2 mm.
*Pedicel color.*—Deep purplish pink N57D.
*Flower petal quantity.*—5.
*Flower petal length.*—1 mm to 2 mm.
*Flower petal width.*—0.5 mm to 2 mm.
*Flower petal shape.*—Deltoid.
*Flower petal apex.*—Acute.
*Flower petal base.*—Truncate.
*Flower petal margin.*—Smooth.
*Flower petal texture.*—Waxy.
*Flower color.*—Red-purple 68B.
*Sepal quantity.*—5.
*Sepal length.*—3.75 mm.
*Sepal width.*—2 mm.
*Sepal shape.*—Ovate.
*Sepal apex shape.*—Aristulate.
*Sepal base shape.*—Truncate.
*Sepal margin shape.*—Smooth.
*Sepal color.*—Yellowish green 145B.
*Sepal texture.*—Densely pubescent.
*Pollinator.*—Not required.

Leaves:
*Length.*—15.5 cm.
*Width.*—4.3 cm.
*Thickness.*—0.5 mm to 0.8 mm.
*Leaf shape.*—Lanceolate.
*Apex shape.*—Acuminate.
*Base shape.*—Cuneate.
*Margin.*—Entire.
*Pubescence.*—Absent.
*Color.*—Young leaf — Light green to light copper brown.
*Color.*—Mature leaf — Upper surface green 139A; lower surface green 141C.
*Venation.*—Primary central vein with herringbone side veins spaced about 8 to 11 mm apart.
*Petiole length.*—Medium, 31 mm.
*Petiole width.*—2 mm to 3 mm.
*Petiole color.*—Yellow-green 146D.
*Thickness of pulvinus.*—3.5 mm to 4.5 mm.
*Leaf orientation.*—Horizontal.
*Aroma of crushed leaves.*—Neutral; turpentine odor absent.

Fruit:
*Weight.*—250 g to 450 g.
*Length.*—121 mm.
*Diameter at widest point.*—91 mm.
*Thickness.*—76 mm.
*Apex.*—Flattened.
*Form of ventral shoulder.*—Rounded upward.
*Form of dorsal shoulder.*—Rounded downward.
*Form of stalk cavity.*—Absent.
*Stalk attachment.*—Strong on immature fruit; medium on mature fruit.
*Stalk length.*—15 cm.
*Stalk diameter.*—4 mm to 5 mm.
*Stalk color.*—Yellow green 154C.
*Beak.*—Small to medium, rounded.
*Skin texture.*—Smooth; medium density lenticels; good resistance to sunburn.
*Skin thickness.*—1.3 to 2.2 mm; tough.
*Skin color of immature fruit.*—Green 135C; red purple 60B blush present on fruit in direct sunlight.
*Skin color of mature fruit.*—Yellow orange 17C to orange N25D, with orange red N30A blush.
*Flesh texture.*—Fine, smooth.
*Flesh color.*—Yellow orange 20A.
*Flavor.*—Sweet with acid balance; pineapple.
*Fiber.*—Not fibrous.
*Fruit sugar content.*—14° Brix and higher.
*Aroma.*—Tropical; no turpentine aroma.
*Fruit per panicle.*—2.

Stone:
*Length.*—7.7 cm.
*Width.*—3.6 cm.
*Depth.*—1.8 cm.
*Weight.*—80 g to 100 g.
*Color.*—Greyed yellow 162C.
*Venation.*—Smooth
*Texture of stone fiber.*—Fine.
*Adherence of fiber to stone.*—Medium.
*Shape of lateral view.*—Oblong.
*Storage.*—Good at 8 to 10° C.
*Susceptibility to bruising.*—Low.
*Susceptibility to wind.*—Low.
*Susceptibility to disease.*—Low.
*Harvest date.*—Mid-late season, just before 'Keitt' mango (not patented); week 11 to 14 in Western Cape, Republic of South Africa.
*Use.*—Fresh market.
*Drought, heat and cold tolerance.*—Tolerant in area tested.

I claim:

1. A new and distinct mango tree substantially as illustrated and described herein.

* * * * *